United States Patent [19]

Lai et al.

[11] Patent Number: 4,639,479
[45] Date of Patent: Jan. 27, 1987

[54] POLYALKYLENEPOLYAMINE HAVING PENDANT SUBSTITUTED OXO-PIPERAZINYLTRIAZINES AND UV LIGHT STABILIZED COMPOSITIONS

[75] Inventors: John T. Lai, Broadview Heights; Pyong N. Son, Akron, both of Ohio

[73] Assignee: The BFGoodrich Company, Akron, Ohio

[21] Appl. No.: 777,999

[22] Filed: Sep. 20, 1985

Related U.S. Application Data

[63] Continuation-in-part of Ser. No. 664,901, Oct. 26, 1984, Pat. No. 4,547,538, which is a continuation-in-part of Ser. No. 350,536, Feb. 2, 1982, Pat. No. 4,480,092.

[51] Int. Cl.[4] ............. C08K 5/34; C07D 251/70; C07D 251/52; C07D 401/14
[52] U.S. Cl. .................... 524/100; 524/96; 544/82; 544/113; 544/198; 544/209
[58] Field of Search ........... 544/82, 113, 198, 209; 524/100, 96

[56] References Cited

U.S. PATENT DOCUMENTS

| 3,919,234 | 11/1975 | Ramey et al. | 544/231 |
| 3,920,659 | 11/1975 | Ramey et al. | 544/231 |
| 4,190,571 | 2/1980 | Lai et al. | 544/357 |
| 4,466,915 | 8/1984 | Lai | 544/344 |
| 4,468,488 | 8/1984 | Minagawa et al. | 544/209 |
| 4,477,615 | 10/1984 | Raspanti et al. | 544/198 |
| 4,480,092 | 10/1984 | Lai et al. | 544/198 |
| 4,547,538 | 10/1985 | Lai et al. | 524/100 |

FOREIGN PATENT DOCUMENTS 8302943 9/1983 PCT Int'l Appl. .......... 544/113

Primary Examiner—Morton Foelak
Assistant Examiner—Kriellion Morgan
Attorney, Agent, or Firm—A. D. Lobo; A. A. Csontos

[57] ABSTRACT

A polyalkylenepolyamine ("PAPA") main chain having pendant substituted 2-oxo-piperazinyl-triazines attached to the N atoms of the PAPA main chain are novel compounds which have highly desirable UV-light stabilizing (UV-S) activity coupled with unexpectedly good thermal stability. These compounds, referred to as "pendant piperazinyl triazines" or P[PIP-T] for brevity, are used in polymer recipes to formulate a stabilized polymeric composition comprising a light-degradable organic polymer containing an effective amount of a P[PIP-T] sufficient to stabilize the polymer. A P[PIP-T] is especially effective in a polyolefin in which there is from about 0.1 percent by weight (% by wt), to about 5% by wt, and is also effective in a wide variety of pastel colored and/or transparent commercially significant polymers.

6 Claims, No Drawings

POLYALKYLENEPOLYAMINE HAVING PENDANT SUBSTITUTED OXO-PIPERAZINYLTRIAZINES AND UV LIGHT STABILIZED COMPOSITIONS

BACKGROUND OF THE INVENTION

This invention is related to the field of stabilizing an organic polymeric material which is particularly to be protected against degradation by ultraviolet (UV) light, by incorporating a UV-stabilizer (UV-S); and, also to the deleterious effects of heat and oxygen by incorporating an antioxidant (AO).

More particularly, the compounds of this invention are relatively high molecular weight (mol wt) hindered amines formed by coupling a polyalkylenepolyamine ("PAPA") which provides the main chain, with a substituted 2-oxo-piperazinyl-triazine ("PIP-T") which provides the pendant groups on the N atoms of the PAPA main chain. These relatively high mol wt compounds are not only excellent photostabilizers but also provide excellent thermal stability.

The PIP-Ts which are disclosed in our U.S. Pat. No. 4,480,092 are formed by coupling a triazine having an appropriate leaving group, typically chlorine, with a polysubstituted piperazinone ("PSP") which is prepared by a ketoform synthesis. The ketoform synthesis (a) with a phase transfer catalyst is disclosed in U.S. Pat. No. 4,167,562; and, (b) without a phase transfer catalyst, in U.S. Pat. No. 4,466,915; pertinent portions of each of which patents are incorporated by reference thereto as if fully set forth herein. The PSP so formed is substituted at the $N^1$ atom of the ring with an alkylamino substituent through which the PSP is subsequently linked to a triazine compound forming a PIP-T.

The PIP-Ts belong to a class of compounds known as multi-ringed triazine derivatives many of which exhibit desirable photostabilization (PS) activity, and more specifically, UV-S activity. However, each has one or more serious drawbacks which makes the one less desirable from a practical, utilitarian point of view than another having a less serious drawback. This reality dictates the unending search, even in the narrow field of multi-ringed triazine derivatives, for compounds with better UV-S activity, and results in discarding numerous derivatives with little or no activity, or those with desirable activity which are impractical to produce economically.

Prior art multi-ringed derivatives with UV-S activity are disclosed in U.S. Pat. Nos. 4,086,204; 4,0051,137; 4,108,829; French Pat. No. 2181 059; and, Japanese Pat. No. 51-4247; inter alia.

Certain cycloalkanes are also known to have UV-S activity, for example those disclosed in Ger. Offen. No. 2,315,042. Highly effective 2-keto-diazacycloalkanes are disclosed in U.S. Pat. Nos. 4,190,571; 4,207,228; substituted piperazinediones are disclosed in U.S. Pat. Nos. 3,919,234; and, 3,920,659.

In particular regard to our '092 patent, we found that a PSP which is distally linked to a triazine nucleus, forming the PIP-T, was unexpectedly effective not only for its UV-S activity, but also for its AO activity, as disclosed in our copending patent application Ser. No. 721,270 filed Apr. 9, 1985. We have now found that this dual activity is enhanced when the PIP-T is hung from a PAPA main chain to form compounds referred to as "pendant PIP-Ts".

The starting material for preparation of the '092 PIP-Ts was a branched chain PAPA which was reductively alkylated. The "branched chain PAPA" used in the preparation of the PSP which was subsequently attached to the triazine ring, was so termed because the C atom adjacent one primary amine group was disubstituted. After reductive alkylation, the compound obtained was cyclized by the ketoform synthesis to yield a PSP in which the $N^1$ of the ring was substituted with an alkylamino chain and the $N^4$ was unsubstituted. When the PIP-T was prepared by displacement of a Cl on the triazine ring, the bridge linking the triazine ring to the diazacycloalkane ring was a polymethylene chain (p methylene groups in the chain) none of which methylene groups was substituted, therefore "unbranched", hence the term "unbranched bridge" to characterize the PIP-Ts herein.

SUMMARY OF THE INVENTION

It has been discovered that a polyalkylenepolyamine ("PAPA") main chain having pendant substituted 2-oxopiperazinyl-triazines attached to the N atoms of the main chain are novel compounds which have highly desirable UV-light stablizing (UV-S) activity coupled with unexpectedly good thermal stability.

It is therefore a general object of this invention to provide a class of compounds comprising acyclic PAPA having a pendant substituent at each nitrogen atom thus forming a PAPA with a pendant triazine nucleus at each N atom; the triazine nucleus is distally linked to a polysubstituted piperazinone (PSP), this combination pendant from the PAPA being referred to herein as the pendant PIP-T (for brevity "P[PIP-T]").

It is also a general object of this invention to provide a stabilized polymeric composition comprising a light-degradable organic polymer containing an effective amount of a P[PIP-T] sufficient to stabilize the polymer.

It is a specific object of this invention to provide a stabilized polymeric composition comprising a polymer of a mono-1-olefin having incorporated therein less than 1 percent by weight (% by wt) of a P[PIP-T].

It has also been discovered that a P[PIP-T] may be used in combination with conventional antioxidants, and with some hindered phenols among these, the combination with each exhibits remarkable activity.

It is therefore a general object of this invention to provide a combination stabilizer for PS and AO stabilization of polymers, particularly polyolefins, in which combination an effective amount of two compounds, one from the class of P[PIP-T] compounds, and the other a hindered phenol selected from the group consisting of tris(3,5-di-t-butyl-4-hydroxybenzyl)isocyanurate commercially available as Goodrite 3114; 2,6-ditertiarybutyl-p-cresol commercially available as "BHT"; 2,2'-ethylidenebis(-4,6-ditertiarybutylphenol) commercially available under the brand Isonox 129; and, octadecyl-3,5-di-t-butyl-4-hydroxybenzenepropionate, is present, each in an amount in the range from 0.1 to about 1 part per 100 parts of polymer (phr).

DETAILED DESCRIPTION OF PREFERRED EMBODIMENTS

The basic structure of the PIP-T compound used to make the P[PIP-T]s of this invention are similar in structure to those of our '092 patent. The PIP-T used in this invention is represented by the following structural formula (I):

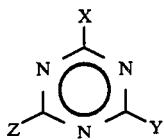

(I)

wherein,

X is a piperazinone substituent having the following formula (II):

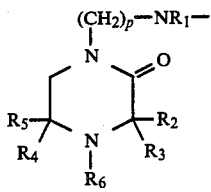

wherein, $R_1$ represents alkyl having 1 to about 24 carbon atoms $C_1$-$C_{24}$, $C_5$-$C_7$ cycloalkyl, $C_7$-$C_{20}$ aralkyl, $C_1$-$C_{24}$ azaalkyl, and $C_6$-$C_{20}$ azacycloalkyl;

$R_2$, $R_3$, $R_4$ and $R_5$ independently represent $C_1$-$C_{24}$ alkyl, and $C_4$-$C_7$ polymethylene which are cyclizable forming a spiro cycloalkylene substituent with the C atom of the piperazinone ring;

$R_6$ represents hydrogen or oxygen, $C_1$-$C_{24}$ alkyl, $C_1$-$C_{12}$ hydroxyalkyl, benzyl, allyl, and $C_1$-$C_{12}$ haloalkyl;

Z represents a radical selected from the group consisting of Cl, OH,

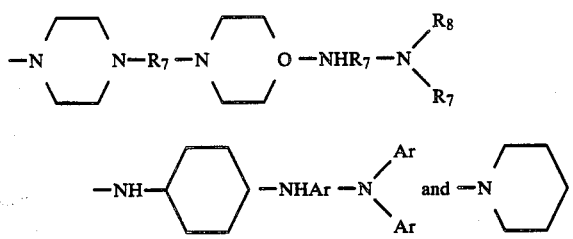

$R_7$ and $R_8$ represent $C_2$-$C_{24}$ alkyl;

Ar represents aryl;

p represents an integer in the range from 2 to 20; and, Y and Z may be the same, or the same as X, provided one of the substituents furnishes a leaving group.

Most preferably, Z is Cl and X and Y are each said piperazinone substituent PSP. When only one of X and Y (say X) is PSP, then Y is preferably selected from the group consisting of OH, $NHC_nH_{2n+1}$, $N(C_nH_{2n+1})_2$,
N—[$CH_2CH(Et)C_4H_9$]$_2$, N—($CH_2$—CH=$CH_2$)$_2$,
$NHCH_2CH(Et)C_4H_9$ N—($C_3H_7$)$_2$

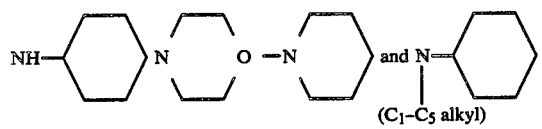

wherein n represents an integer in the range from 1 to about 6.

Particular monomeric PIP-T compounds used in the preparation of P[PIP-T]s are represented by the foregoing formula (I) whereiin one of the substituents is a leaving group and at least one of the other substituents is a polysubstituted pierazinone.

The basic structure of the P[PIP-T] stabilizer compounds of this invention is represented by the following structural formula (IV):

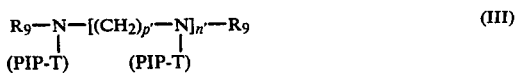

and more fully,

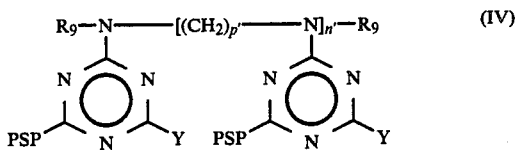

wherein, p' is an integer in the range from 2 to 8;

n' is an integer in the range from 2 to 12; and, $R_9$ represents H, $C_1$-$C_{24}$ alkyl, $C_4$-$C_7$ cycloalkyl; $C_1$-$C_{12}$ cyanoalkyl or hydroxyalkyl, and phenyl; and, PSP and Y have the same connotation as hereinabove.

It is especially significant that theses relatively high mol wt compounds contain an unbranched bridge which distally links the PSP to a triazine moiety, and only these, namely the PSP and the triazine may independently be substituted. (Note that the term "bridge" is used to identify the connection betwen the triazine ring and the PAPA, while the term "main chain" is used to identify the structure of the PAPA). The polymethylene bridge is not substituted because of the manner in which the PSP is derived. The substituents on the PSP and the triazine, along with the length of the bridge may be varied to produce compounds which are readily coupled to PAPA main chain, so as to yield P[PIP-T]s which not only have desirable PS properties, but good heat and oxidation stabilizing properties, complemented with suitable solubility and dispersability.

The P[PIP-T]s are generally solids, and soluble or partially soluble in acetone, diethyl ether, dioxane, tetrahydrofuran, carbon tetrachloride, chloroform, lower primary alcohols having from 1 to about 5 C atoms such as methanol, ethanol and propanol, aromatic hydrocarbons such as benzene and toluene, but much less soluble in aliphatic hydrocarbons such as hexane. P[PIP-T]s are generaly insoluble in water. They are white when pure.

The amount of stabilizer employed will vary with the particular material to be stabilized and also the substituents used. Generally however, for effective UV stabilization of organic materials, an amount of the P[PIP-T] used is in the range from about 0.01% by wt to about 10% by wt, based on the wt of organic material. In typical stabilized synthetic resinous materials, the amount of P[PIP-T] used is in the range from about 0.01 to about 5% by wt.

Compositions of this inventions are the stabilized materials which combat the deleterious effects of uv light, thermal or oxidative degradation such as are usually evidenced by discoloration and/or embrittlement. These compositions generally benefit from the inclusion of additional secondary stabilizers to achieve even greater stability against a combination of actinic light, heat and oxygen. Therefore, in conjunction with the stabilizers of this invention, compositions may include secondary stabilizers which may be present in the range from about 0.01 to about 10 phr, and preferably from about 0.1 to about 5 phr of the organic continuous phase. Several types of known secondary stabilizers may be used, such as those disclosed in U.S. Pat. Nos. 3,325,448; 3,769,259; 3,920,659; 3,962,255; 3,966,711; 3,971,757; inter alia.

Organic materials which may be stabilized against uv light, thermal and oxidative degradation, include copolymers of butadiene with acrylic acid, alkyl acrylates or methacrylates, polyisoprene, polychloroprene, and the like; polyurethanes; vinyl polymers known as PVC resins such as polyvinyl chloride, copolymers of vinyl chloride with vinylidene chloride, copolymers of vinyl halide with butadiene, styrene, vinyl esters, and the like; polyamides such as those derived from the reaction of hexamethylene diamine with adipic or sebacic acid; epoxy resins such as those obtained from the condensation of epichlorohydrin with bisphenols, and the like; ABS resins, polystyrene, polyacrylonitrile, polymethacrylates, polycarbonates, varnish, phenol-formaldehyde resins, polyepoxides, polyesters, and polyolefin homo and copolymers such as polyethylene, polypropylene, ethylene-propylene polymers, ethylene-propylenediene polymers, ethylene vinyl acetate polymers and the like. The P[PIP-T] compounds can also be used to stabilize mixtures and blends of polymeric materials such as ABS resin blends, PVC and polymethacrylate blends, and blends of homopolymers and copolymers such as blends of polypropylene in EPDM polymers.

Most particularly, the P[PIP-T]s are especially useful as uv-light stabilizers for synthetic resinous materials used in the form of fibers, or in thermoformed shapes which are at least partially permeable to visible light, and particularly for those which are transparent thereto, such as polyvinylaromatics and polyolefins.

Many known compoundng ingredients may be used along with the P[PIP-T]s in the compositions. Such ingredients include metal oxides such as zinc, calcium and magnesium oxide, fatty acids such as stearic and lauric acid, and salts thereof such as cadmium, zinc and sodium stearate and lead oleate, fillers such as calcium and magnesium carbonate, calcium and barium sulfates, aluminum silicates, asbestos and the like; plasticizers and extenders such as dialkyl and diaryl organic acids like diisobutyl, diisooctyl, diisodecyl, and dibenzyl oleates, stearates, sebacates, azelates, phthalates, and the like; ASTM type 2 petroleum oils, paraffinic oils, castor oil, tall oil, glycerin and the like.

Particularly desirable secondary stabilizers are one or more antioxidants used in the range from about 0.01 phr to about 20 phr, preferably from about 0.1 to about 5 phr of the material to be stabilized. Of the types of antioxidants used, are phosphite, phosphate, sulfide and phenolic antioxidants, the last being preferred. Most preferred are the hindered phenol AOs specified hereinabove, though others are also useful such as 2,6-di-t-butyl-paracresol; 2,2'-methylene-bis(6-t-butyl-phenol); 2,2'-thiobis(4-methyl-6-t-butylphenol); 2,2'-methylene-bis(6-t-butyl-4-ethyl-phenol); 4,4'-butylidene-bis(6-t-butyl-m-cresol); 2-(4-hydroxy-3,5-di-t-butylanilino)-4,6-bis(octylthio)-1,3,5-triazine; benzenepropanoic acid, 3,5-bis(1,1-dimethylethyl)-4-hydroxy-,(2,4,6-trioxo-1,3,5-triazine-1,3,5(2H,4H,6H)-triyl)tri-2,1-ethanediyl ester (Goodrite ®3125); tetrakis[methylene 3-(3',5'-di-t-butyl-4'-hydroxyphenyl)propionate]methane; and particularly commercially available antioxidants such as Irganox 1010, 1035, 1076 and 1093. Other ingredients such as pigments, tackifiers, flame retardants, fungicides, and the like may also be added.

The P[PIP-T]s, and other compounding ingredients if used, can be admixed witn the material to be stabilized using known mixing techniques can equipment such as internal mixing kettles, a Banbury mixer, a Henschel mixer, a two-roll mill, an extruder mixer, or other standard equipment, to yield a composition which may be extruded, presed, blowmolded or the like into film, fiber or shaped articles. Usual mixing times and temperatures can be employed which may be determined with a little trial and error for any particular composition. The objective is to obtain intimate and uniform mixing of the components. A favorable mixing procedure to use when adding a P[PIP-T] to an organic material is either to dissolve or suspend the P[PIP-T] in a liquid such as methylene chloride before adding it, or to add the P[PIP-T] directly to the polymeric material whether the P[PIP-T] is in the form of a powder or oil, or to extruder-mix the P[PIP-T] and material prior to forming the product.

The UV-stability of a stabilized composition can be evaluated by exposing a prepared sample of the composition to Xenon or carbon arc light in a Weather-O-Meter (ASTM D2569-79) operating at a temperature of about 145° F. (63° C.) at about 50% relative humidity. Degradation of the sample is monitored by periodically measuring the tensile strength after exposure, and the hydroperoxide absorption band at 3460 cm$^{-1}$ or carbonyl absorptionband at 1720 cm$^{-1}$ using an IR spectrophotometer. The rapid formation of carbonyl indicates failure of the sample. The test procedure is well known, and is published in the text *Photodegradation, Photooxidation and Photostabilization of Polymers* by Ranby and Rabek, John Wiley & Sons, N.Y., N.Y. (1975), at pg 129 et seq., and is disclosed in U.S. Pat. No. 3,909,493. Failure of the sample is also checked by visual signs of cracking when the sample is bent 180°. Degradation of fibers is checked by suspending lengths of fiber spaced about 0.125" apart on a stainless steel holder and testing three of them periodically until it is found that they suffer a 50% loss of initial tensile strength (ASTM D2343-67).

Samples of the compositions are also checked for oxidative and thermal stability by measuring the time to discoloration and/or embrittlement of the sample after aging in an air circulating oven at 125° C. (ASTM D1204-78), and other standard tests. These tests include tests for resistance to water extraction, perchloroethylene extraction, and "gas fade" as will be explained in greater detail hereinafter.

Preparation of polysubstituted piperazinone ("PSP"):

A PSP is typically prepared as described in our '092 patent. For example, a particular PSP(1), namely 1-[2-(2-butylamino)ethyl]-3,5,5-trimethyl-3-ethyl-2-piperazinone having the following structure

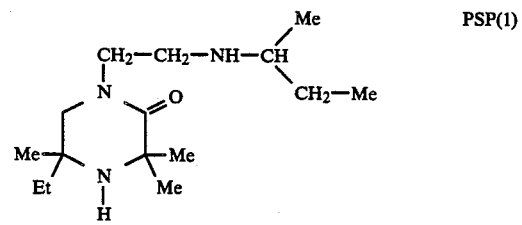

is prepared by reacting N-(1-methylpropyl)-N'-(2-amino-2-methylpropyl)-1,2-ethanediamine, 2-butanone and chloroform in dichloromethane in the presence of 18-Crown-6 polyether phase transfer catalyst.

In an analogous manner, by reaction with N-(1,3-dimethylbutyl)-N'-(2-amino-2-methylpropyl)-1,2-ethanediamine, acetone and chloroform, a PSP(2) having the following structure is obtained:

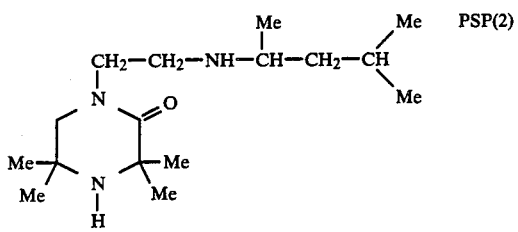

In an analogous manner, by reaction with N-(2-amino-2-methylpropyl)-N'-(cyclohexyl)-1,2-ethanediamine, acetone, and chloroform in ethylene chloride, a PSP(3) having the following structure is obtained:

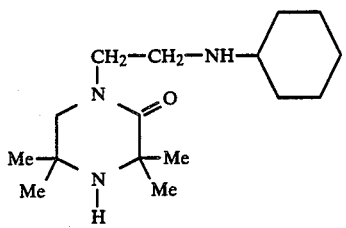

In an analogous manner, by reaction with N-(2-amino-2-methylpropyl)-N'-(cyclohexyl)-1,3-propanediamine, acetone, and chloroform in ethylene chloride, a PSP(4) having the following structure is obtained:

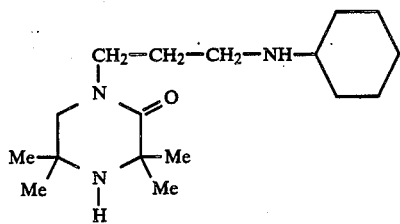

Preparation of PIP-T:

The PSP obtained is then coupled by displacement of a suitable leaving group, preferably Cl, of a reactive triazine compound. For example, a particular PIP-T(1) namely, 1,1'-[(6-chloro-1,3,5-triazine-2,4-diyl)bis[[(1-methylpropyl)imino]-2,1-ethanediyl]]bis[3,3,5-trimethyl-3-ethyl-2-piperazinone] having the following structure

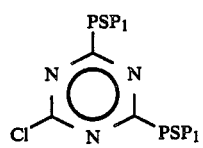

wherein PSP$_1$ represents

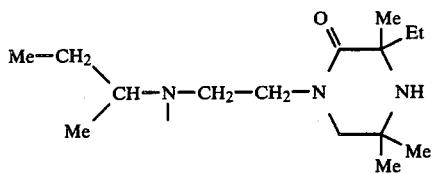

the residue of PSP(1)

PIP-T(1) is prepared by reacting 2 moles of PSP(1) with 1 mole of cyanuric chloride dissolved in acetone and diluted with water, in the presence of sodium carbonate, as described in our '092 patent.

In an analogous manner, PIP-T(2) is prepared by the reaction of PSP(2) with cyanuric chloride, and PIP-T(3) and PIP-T(4) are each prepared by the reaction of PSP(3) and PSP(4) respectively with cyanuric chloride. The foregoing PIP-Ts have the following structures:

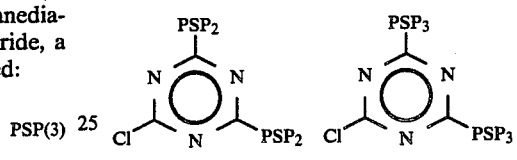

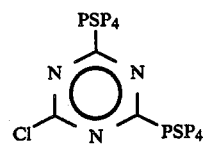

PIP-T(4)

wherein PSP$_2$, PSP$_3$ and PSP$_4$ are each the residues of PSP(2), PSP(3) and PSP(4) respectively.

Preparation of a P[PIP-T] in which (and the code indicates that) a main chain PAPA is provided with a PIP-T substituent on the N atoms in the PAPA's main chain:

A P[PIP-T] having from 3 to 8 N atoms in the PAPA main chain, and from 2 to 3 C atoms intermediate each N atom in the chain, may be prepared by reaction of an appropriate PAPA with a PIP-T having a reactive leaving group which will be displaced by an amine in the PAPA chain. The general structure of a PAPA used to form the P[PIP-T] is:

$$NHR_9-[(CH_2)_{p'}-NH]_{n''}-R_9 \qquad V$$

wherein,
R$_9$ has the same connotation as hereinabove;
p' is an integer in the range from 2 to 8; and,
n'' is an integer in the range from 2 to about 12.

The general structure of the P[PIP-T] formed is:

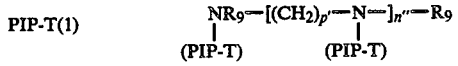

A particular P[PIP-T] in which the substituent is PIP-T(1) and the PAPA is N-(2-aminoethyl)-1,2-ethanediamine is identified as "P[PIP-T(1)]" having the following structure:

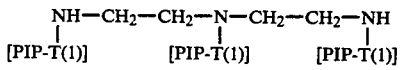

VII wherein [PIP-T(1)] is the residue of PIP-T(1). The foregoing P[PIP-T] having the struture VII is identified herein as P[PIP-T]VII, and more fully identified as: 1,1',1'',1'''-[[[4,6-bis[(1-methylpropyl)[2-(3,5,5-trimethyl-3-ethyl-2-oxo-1-piperazinyl)ethyl]amino]-1,3,5-triazin-2-yl]imino]bis[2,1-ethanediylimino-1,3,5-triazine-6,2,4-triylbis[[(1-methylpropyl)imino]-2,1-ethanediyl]]]tetrakis[3,5,5-trimethyl-3-ethylpiperazinone] is as follows:

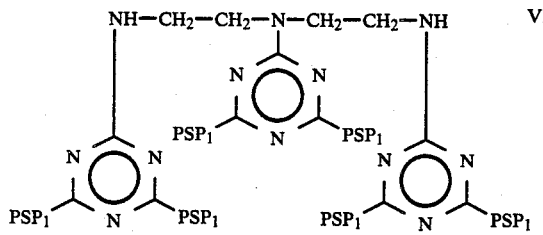

VIIa wherein PSP₁ represents the residue of PSP(1).

EXAMPLE 1

Preparation of P[PIP-T]VII:

In a 110 mL autoclave were charged 6.5 g (0.010 mole) of 1,1'-[(6-chloro-1,3,5-triazine-2,4-diyl)bis[[(1-methylpropyl)imino]-2,1-ethanediyl]]bis [3,5,5-trimethyl-3-ethyl-2-piperazinone], 0.34 g (0.0033 mole) of N-(2-aminoethyl)-1,2-ethanediamine, 70 mL toluene, and 2.0 g of 20% aqueous NaOH solution. The mixture was reacted at 180° C. for 20 hr and then cooled. The cooled mixture was washed three times with 50 mL portions of water. The organic layer was stripped to obtain 4.6 g of solid which melts at 135° C. The structure was confirmed by IR and mass spectroscopic data.

EXAMPLE 2

Another P[PIP-T], represented by the structure (VIII) in which the substituent is PIP-T(3) and the PAPA is N-(2-aminoethyl)-1,2-ethanediamine, is identified as "P[PIP-T]VIII" and has the following structure:

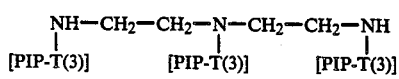

VIII wherein [PIP-T(3)] is the residue of PIP-T(3). The particular P[PIP-T]VIII is more fully identified as: 1,1',1'',1'''-[[[4,6-bis[cyclohexyl[2-(3,3,5,5-tetramethyl-2-oxo-1-piperazinyl)ethyl]amino]-1,3,5-triazin-2-yl]imino]bis[2,1-ethanediylimino-1,3,5-triazine-6,2,4-triylbis[[(cyclohexyl)imino]-2,1-ethanediyl]]]tetrakis[3,3,5,5-tetramethylpiperazinone] and has the following structure:

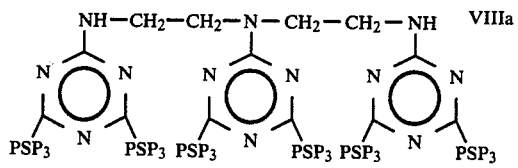

VIIIa wherein, PSP₃ represents the residue of PSP(3).

Preparation of P[PIP-T]VIII:

In a 110 mL autoclave were charged 4.05 g (0.006 mole) of 1,1'-[(6-chloro-1,3,5-triazine-2,4-diyl)bis[[cyclohexyl)imino]-2,1-ethanediyl]]bis[3,3,5,5-tetramethylpiperazinone], 0.21 g (0.002 mole) of N-(2-aminoethyl)-1,2-ethanediamine, 50 mL toluene, and 1.2 g of 20% aqueous NaOH solution. The mixture was reacted at 180° C. for 20 hr and then cooled. After a work-up analogous to that in the previous example, 3.3 g of solid which melts at 158° C. was isolated. The structure was confirmed by IR and mass spectroscopic data.

EXAMPLE 3

In an analogous manner a P[PIP-T]IX is prepared having the structure IX:

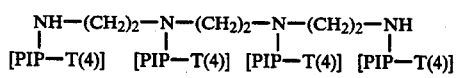

IX or,

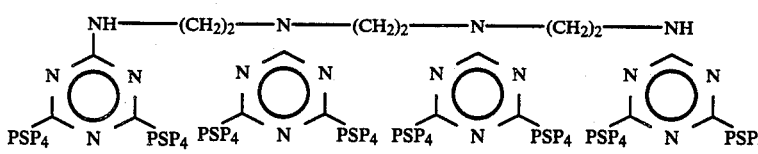

IXa wherein PSP₄ represents

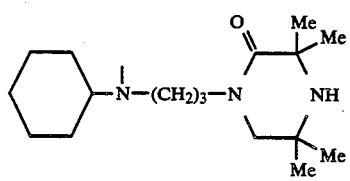

The P[PIP-T]IX is more fully identified as: 1,1',1'',1'''-[1,2-ethanediylbis[[[2-[[4,6-bis[cyclohexyl[3-(3,3,5,5-tetramethyl-2-oxo-1-piperazinyl)propyl]amino]-1,3,5-triazin-2-yl]amino]ethyl]imino]][1,3,5-triazine-6,2,4-triyl]bis[(cyclohexylimino)-3,1-propanediyl]]]tetrakis[3,3,5,5-tetramethylpiperazinone]
The m p of the compound is 101°–106° C.

EXAMPLE 4

In an analogous manner, another compound P[PIP-T]X having the following structure X is prepared:

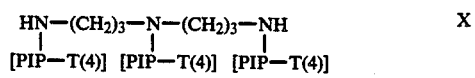

X

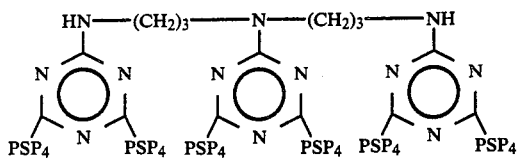

wherein PSP₄ is the residue of PSP(4).

The P[PIP-T]X is more fully identified as: 1,1',1",1'''-[[[4,6-bis[cyclohexyl[3-(3,3,5,5-tetramethyl-2-oxo-1-piperazinyl)propyl]amino]-1,3,5-triazin-2-yl]imino]bis[3,1-propanediylimino-1,3,5-triazine-6,2,4-triylbis[[(cyclohexyl)imino]-3,1-propanediyl]]]-tetrakis[3,3,5,5-tetramethylpiperazinone].

EXAMPLE 5

Yet another compound P[PIP-T]XI having the structure XI is prepared in an analogous manner:

$$\begin{array}{c} NH-(CH_2)_2-N-(CH_2)_2-NH \\ | \qquad | \qquad | \\ [PIP-T(4)] \quad [PIP-T(4)] \quad [PIP-T(4)] \end{array} \quad XI$$

or,

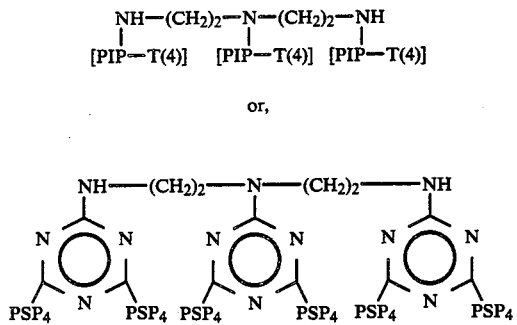

wherein PSP₄ represents the residue of PSP(4).

P[PIP-T]XI is more fully identified as follows: 1,1',1",1'''-[[[4,6-bis[cyclohexyl[3-(3,3,5,5-tetramethyl-2-oxo-1-piperazinyl)propyl]amino]-1,3,5-triazin-2-yl]imino]bis[2,1-ethanediylimino-1,3,5-triazine-6,2,4-triylbis[[(cyclohexyl)imino]-3,1-propanediyl]]]tetrakis[3,3,5,5-tetramethylpiperazinone]

The m p of the compound is 146° C.

EXAMPLE 6

Still another compound P[PIP-T]XII having the structure XII herebelow is prepared in an analogous manner:

$$\begin{array}{c} NH-(CH_2)_2-N-(CH_2)_2-NH \\ | \qquad | \qquad | \\ [PIP-T(4)R] \quad [PIP-T(4)R] \quad [PIP-T(4)R] \end{array} \quad XII$$

or,

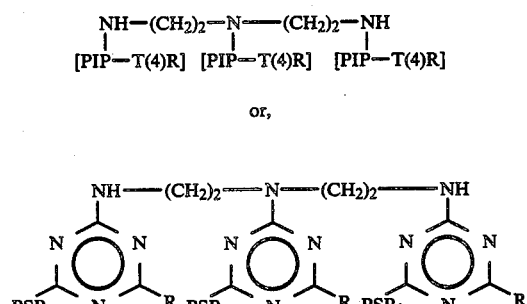

wherein R represents

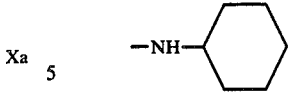

and PSP₄ has the same structure given above.

The P[PIP-T]XII is more fully identified as follows: 1,1'-[[[4-(cyclohexylamino)-6-[cyclohexyl[3-(3,3,5,5-tetramethyl-2-oxo-1-piperazinyl)propyl]amino]-1,3,5-triazin-2-yl]imino]bis[2,1-ethanediylimino[6-(cyclohexylamino)-1,3,5-triazine-4,2,-diyl]cyclohexylimino(3,1-propanediyl)]]bis[3,3,5,5-tetramethylpiperazinone]. The m p of the compound was 125°–134° C.

EXAMPLE 7

Yet another compound P[PIP-T]XIII having the structure XIII herebelow is prepared in an analogous manner:

$$\begin{array}{c} NH-(CH_2)_2-N-(CH_2)_2-NH \\ | \qquad | \qquad | \\ [PIP-T(2)] \quad [PIP-T(2)] \quad [PIP-T(2)] \end{array} \quad XIII$$

or,

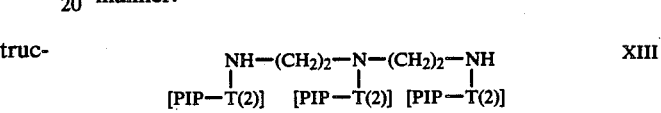

wherein PSP₂ represents

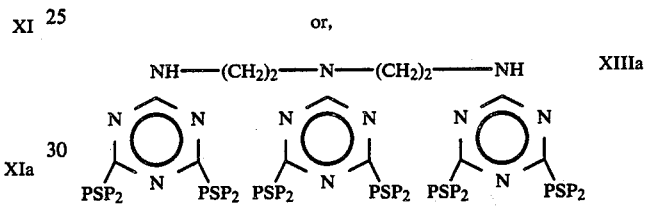

P[PIP-T]XIII is more fully identified as follows: 1,1',1",1'''-[[[4,6-bis[(1,3-dimethylbutyl)[2-(3,3,5,5-tetramethyl-2-oxo-1-piperazinyl)ethyl]amino]-1,3,5-triazin-2-yl]imino]bis[2,1-ethanediylimino-1,3,5-triazine-6,2,4-triylbis[[1,3-dimethylbutyl)imino]-2,1-ethanediyl]]]tetrakis[3,3,5,5-tetramethylpiperazinone]. The compound has a m p of 90° C.

The following Table I sets forth data obtained in tests conducted with 2 mil thickness samples of polypropylene. The blank and each sample includes 0.05 phr of Goodrite ®3125 antioxidant, and the amount of stabilizer used in each sample is 0.1 phr. Oven aging is done at 125° C. in the standard test procedure, and the Weather-O-Meter tests give the number of hours after which a sample loses 50% of its original tensile strength. Chimassorb 944 is a commercially available polytriazine having piperidine substituents disclosed in U.S. Pat. No. 4,086,204.

TABLE I

| Stabilizer | Oven aging (days) | Xenon Weather-O-Meter (hr) Extraction with water | |
|---|---|---|---|
| | | Before | After |
| Blank | | | |
| Chimassorb 944 | 25 | 1720 | 1040 |
| P[PIP-T]VII | 33 | 1280 | 920 |

TABLE I-continued

| Stabilizer | Oven aging (days) | Xenon Weather-O-Meter (hr) Extraction with water | |
|---|---|---|---|
| | | Before | After |
| P[PIP-T]VIII | 98 | 1400 | 1210 |

Table II herebelow sets forth data obtained in oven aging and photostabilization tests conducted with yarn made of Profax 6301 polypropylene which consists of 40 filaments (approx 10 denier) for a total of 400–500 denier per yarn. Each piece of yarn (or 'fiber') including the blank, contained 0.1 phr Ca stearate, and 0.2 part P[PIP-T] which is identified by code.

Oven aging is done at 125° C. in a convection oven in a conventional manner except that samples are rotated manaually, daily. In this oven aging test, loops of yarn are suspended in an oven which substantially meets the requirements of ASTM D3012-79. A loop is removoed from the oven every couple of days and tested for tensile strength. When the tensile is one-half ($\frac{1}{2}$) the original tensile, the sample is deemed to have failed.

Photostabilization is measured by Xenon Weather-O-Meter tests conducted with samples each of which consists of 30 or 40 slightly spaced-apart turns of filament on a stainless steel holder. A 2" long piece of fiber (in triplicate) is removed every 300 hr and tested for tensile. When the tensile is $\frac{1}{2}$ the original tensile, the sample is deemed to have failed.

TABLE II

| Stabilizer | Xenon W'er-O-Meter (hr) | Oven Aging (days) |
|---|---|---|
| P[PIP-T]VIII | 1260 | 16 |
| P[PIP-T]X | 1340 | 13 |
| P[PIP-T]XII | 1310 | 10 |
| Chimassorb 944 | 1350 | 5 |

The most preferred utility for the compounds of this invention is in film, fiber and other shaped articles of the commercially important resins, many of which are pigmented or dyed with conventional relatively light colors, particularly pastel shades. Many of the compounds of this invention do not interfere with the color imparted by the pigment or dye, yet provide the desired stabilization, which is a highly merchantable trait.

We claim:

1. A class of compounds comprising acyclic polyalkylenepolyamines ("PAPA") having a pendant substituent at each N atom to form a PAPA with a pendant triazine nucleus at each nitrogen atom to form a pendant piperazinone-triazine ("P[PIP-T]") having the structure $$R_9-N-[(CH_2)_{p'}-N]_{n'}-R_9$$
$$\quad\;\; | \qquad\qquad\;\; |$$
$$\;(PIP-T) \quad\;\; (PIP-T)$$

wherein
p' is an integer in the range from 2 to 8; $R_9$ represents H, $C_1$–$C_{24}$ alkyl, $C_4$–$C_7$ cycloalkyl; $C_1$–$C_{12}$ cyanoalkyl or hydroxyalkyl, and phenyl;
n' is an integer in the range from 2 to 12; (PIP-T) is represented by the residue of

[Structure: (PSP) with triazine ring having Y and Z substituents]

wherein, PSP is a substituent having the formula

[Structure: piperazinone with $(CH_2)_p$–$NR_1$–, $R_2$, $R_3$, $R_4$, $R_5$, $R_6$ substituents]

wherein,
$R_1$ represents alkyl having 1 to about 24 carbon atoms ($C_1$–$C_{24}$), $C_5$–$C_7$ cycloalkyl, $C_7$–$C_{20}$ aralkyl, $C_1$–$C_{24}$ azaalkyl, and $C_6$–$C_{20}$ azacycloalkyl;
$R_2$, $R_3$, $R_4$ and $R_5$ independently represent $C_1$–$C_{24}$ alkyl, and $C_4$–$C_7$ polymethylene which are cyclizable forming a spiro cycloalkylene substituent with the C atom of the piperazinone ring;
$R_6$ represents hydrogen or oxygen, $C_1$–$C_{24}$ alkyl, $C_1$–$C_{12}$ hydroxyalkyl, benzyl, allyl, and $C_1$–$C_{12}$ haloalkyl;
Y may be the same as (PSP) or Z;
Z represents a radical selected from the group consisting of Cl, OH,

[Structures: –N(piperazine)N–$R_7$–N(piperazine), O–NH$R_7$–N($R_7$)($R_8$), –NH(cyclohexyl)–NHAr, –N(Ar)(Ar), and –N(piperidine)]

$R_7$ and $R_8$ represent $C_2$–$C_{24}$ alkyl;
Ar represents aryl;
p represents an integer in the range from 2 to 20;
and, Y and Z may be the same, or the same as X provided one of the substituents furnishes a leaving group.

2. The compounds of claim 1 wherein PIP-T is represented by the structure:

[Structure: triazine with (PSP), (PSP), and Z substituents]

wherein Z represents Cl.

3. The compounds of claim 1 wherein: PIP-T is represented by the structure

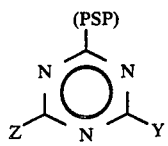

wherein

Z represents Cl; and,

Y is selected from the group consisting of OH, NHC$_n$H$_{2n+1}$, N(C$_n$H$_{2n+1}$)$_2$, N—[CH$_2$CH(Et)C$_4$H$_9$]$_2$, N—(CH$_2$—CH=CH$_2$)$_2$, NHCH$_2$CH(Et)C$_4$H$_9$ N—(C$_3$H$_7$)$_2$

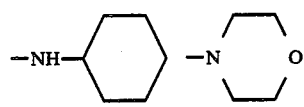

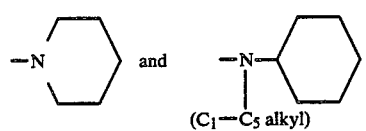

wherein n represents an integer in the range from 2 to about 6.

4. The compounds of claim 1 wherein: PSP is the residue of a polysubstituted piperazinone selected from the group consisting of compounds having the structures:

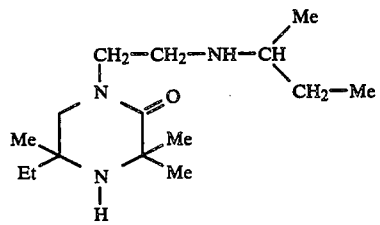
PSP(1)

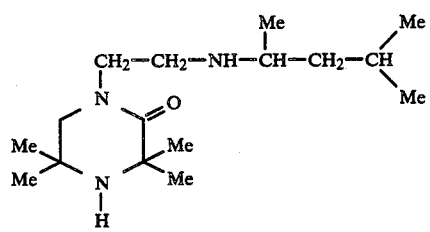
PSP(2)

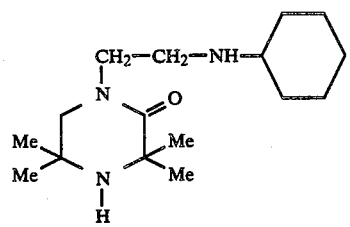
PSP(3)

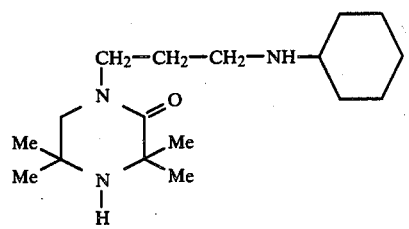
PSP(4)

5. The compounds of claim 1 including:

(i)  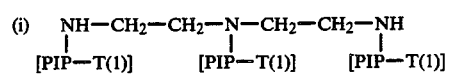
VII 1,1′,1″, 1‴-[[[4,6-bis[(1-methylpropyl)[2-(3,5,5-trimethyl-3-ethyl-2-oxoD-1-piperazinyl)ethyl]amino]-1,3,5-triazin-2-yl]imino]bis[2,1-ethanediylimino-1,3,5-triazine-6,2,4-triylbis[[(1-methylpropyl)imino]-2,1-ethanediyl]]]tetrakis[3,5,5-trimethyl-3-ethylpiperazinone];

(ii) 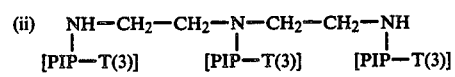
VIII 1,1′,1″, 1‴-[[[4,6-bis[cyclohexyl[2-(3,3,5,5,-tetramethyl-2-oxo-1-piperazinyl)ethyl]amino]-1,3,5-triazin-2-yl]-imino]bis[2,1-ethanediylimino-1,3,5-triazine-6,2,4-triylbis[[(cyclohexyl)imino]-2,1-ethanediyl]]-]tetrakis[3,-3,5,5-tetramethylpiperazinone];

(iii) 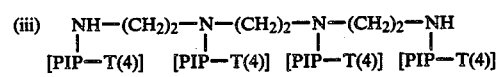
IX 1,1′,1″, 1‴-[1,2-ethanediylbis[[[2-[[4,6-bis[cyclohexyl-[3-(3,-3,5,5-tetramethyl-2-oxo-1-piperazinyl)propyl]-amino]-1,3,5-triazin-2-yl]amino]ethyl]imino][1,3,5-triazine-6,2,4-triyl]bis[(cyclohexylimino)-3,1-propanediyl]]]tetrakis[3,-3,5,5-tetramethylpiperazinone];

(iv) 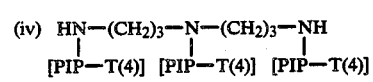
(X)

1,1′,1″, 1‴-[[[4,6-bis[cyclohexyl[3-(3,3,5,5-tetramethyl-2-oxo-1-piperazinyl)propyl]amino]-1,3,5-triazin-2-yl]imino]bis[3,1-propanediylimino-1,3,5-triazine-6,2,4-triylbis[[(cyclohexyl)imino]-3,1-propanediyl]]]-tetrakis[3,3,5,5-tetramethylpiperazinone];

(v) 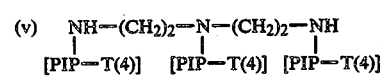
XI 1,1′,1″, 1‴-[[[4,6-bis[cyclohexyl[3-(3,3,5,5-tetramethyl-2-oxo-1-piperazinyl)propyl]amino]-1,3,5-triazin-2-yl]imino]bis[2,1-ethanediylimino-1,3,5-triazine-6,2,4-triylbis[[(cyclohexyl)imino]-3,1-propanediyl]]]tetrakis[3,3,5,5-tetramethylpiperazinone];

(vi)

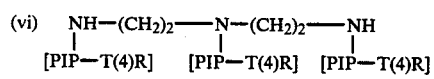
$$[PIP-T(4)R] \quad [PIP-T(4)R] \quad [PIP-T(4)R]$$

XII 1,1'-[[[4-(cyclohexylamino)-6-[cyclohexyl[3-(3,3,5,5-tetramethyl-2-oxo-1-piperazinyl)propyl]amino]-1,3,5-triazin-2-yl]imino]bis[2,1-ethanediylimino[6-(cyclohexylamino)-1,3,5-triazine-4,2,-diyl]cyclohexylimino(3,1-propanediyl)]]bis[3,3,5,5-tetramethylpiperazinone]; and, (vii)

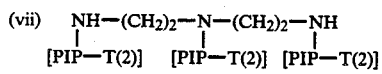
$$[PIP-T(2)] \quad [PIP-T(2)] \quad [PIP-T(2)]$$

XIII 1,1',1'',1'''-[[[4,6-bis[(1,3-dimethylbutyl)[2-(3,3,5,5-tetramethyl-2-oxo-1-piperazinyl)ethyl]amino]-1,3,5-triazin-2-yl]imino]bis[2,1-ethanediylimino-1,3,5-triazine-6,2,4-triylbis[[1,3-dimethylbutyl)imino]-2,1-ethanediyl]]]tetrakis[3,3,5,5-tetramethylpiperazinone].

6. An organic polymeric composition of matter resistant to degradation by ultraviolet light said composition having dispersed therein from about 0.01 part to about 5 parts by weight of a stabilizer compound consisting of an acyclic polyalkylene polyamine having substituted at the N atoms thereof a polysubstituted piperazinone distally linked to a triazine nucleus, per 100 parts of said organic material, said stabilizer compound being represented by the structural formula $$R_9-N-[(CH_2)_{p'}-N]_{n'}-R_9$$
$$\quad | \quad\quad\quad\quad | $$
$$(PIP-T) \quad\quad (PIP-T)$$

wherein p' is an integer in the range from 2 to 8; $R_9$ represents H, $C_1$-$C_{24}$ alkyl, $C_4$-$C_7$ cycloalkyl; $C_1$-$C_{12}$ cyanoalkyl or hydroxyalkyl, and phenyl;

n' is an integer in the range from 2 to 12; (PIP-T) is represented by the residue of

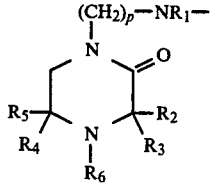

wherein, PSP is a substituent having the formula

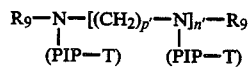

wherein, $R_1$ represents alkyl having 1 to about 24 carbon atoms ($C_1$-$C_{24}$), $C_5$-$C_7$ cycloalkyl, $C_7$-$C_{20}$ aralkyl, $C_1$-$C_{24}$ azaalkyl, and $C_6$-$C_{20}$ azacycloalkyl;

$R_2$, $R_3$, $R_4$ and $R_5$ independently represent $C_1$-$C_{24}$ alkyl, and $C_4$-$C_7$ polymethylene which are cyclizable forming a spiro cycloalkylene substituent with the C atom of the piperazinone ring;

$R_6$ represents hydrogen or oxygen, $C_1$-$C_{24}$ alkyl, $C_1$-$C_{12}$ hydroxyalkyl, benzyl, allyl, and $C_1$-$C_{12}$ haloalkyl;

Z represents a radical selected from the group Z consisting of Cl, OH,

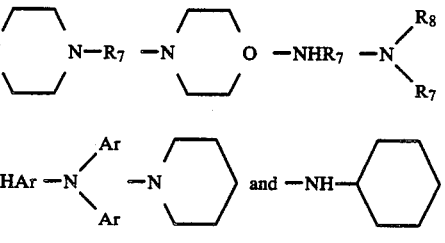

$R_7$ and $R_8$ represent $C_2$-$C_{24}$ alkyl;

Ar represents aryl;

p represents an integer in the range from 2 to 20; and,

Y and Z may be the same, or the same as X, provided one of the substituents furnishes a leaving group.

* * * * *